United States Patent [19]

Schuman et al.

[11] 3,954,758

[45] May 4, 1976

[54] PROCESS FOR FLUORINATING URACIL AND DERIVATIVES THEREOF

[75] Inventors: Paul D. Schuman, Hawthorne; Paul Tarrant, Gainesville; Dale A. Warner, Gainesville; Geraldine Westmoreland, Gainesville, all of Fla.

[73] Assignee: PCR, Inc., Gainesville, Fla.

[22] Filed: Oct. 4, 1971

[21] Appl. No.: 186,444

Related U.S. Application Data

[63] Continuation-in-part of Ser. No. 41,719, May 27, 1970, abandoned, which is a continuation of Ser. No. 709,797, March 1, 1968, abandoned, which is a continuation-in-part of Ser. No. 658,645, Aug. 7, 1967, abandoned.

[52] U.S. Cl. ............................... 260/260; 260/257; 424/251; 424/254
[51] Int. Cl.² ............... C07D 239/54; C07D 239/62
[58] Field of Search ........................... 260/260, 257

[56] References Cited

UNITED STATES PATENTS 3,277,092  10/1966  Duschinsky et al. ............. 260/256.4
3,682,917  8/1972  Knuniants et al. ................ 260/260

OTHER PUBLICATIONS

Wang, Journal of Organic Chemistry 24, 11–13 (1959).

*Primary Examiner*—Paul M. Coughlan, Jr.
*Attorney, Agent, or Firm*—Murray and Whisenhunt

[57] ABSTRACT

Direct fluorination of uracil and its derivatives, in the presence of an aqueous solvent, by fluorine gas to produce 5-fluorouracil and 5-fluorouracil derivatives is disclosed. Novel compounds produced by the reaction, such as 5,5-difluoro-6-hydroxy-5,6-dihydrouracil are also disclosed. The derivatives of 5-fluorouracil are useful as germicidal agents while 5-fluorouracil itself is a known cancer chemotherapy agent.

10 Claims, No Drawings

PROCESS FOR FLUORINATING URACIL AND DERIVATIVES THEREOF

CROSS-REFERENCE TO RELATED APPLICATIONS

This is a continuation-in-part of our abandoned application Ser. No. 41,719 filed May 27, 1970, which in turn was a streamlined continuation of our now abandoned application Ser. No. 709,797, filed Mar. 1, 1968, which is a continuation-in-part of our now abandoned application Ser. No. 658,645, filed Aug. 7, 1967.

BACKGROUND OF THE INVENTION

The present invention relates to a novel process for preparing uracil derivatives and novel chemical compounds so produced.

Uracil has been reacted with various compounds to achieve substitution in the 5 position, see "Chlorination of 2,4-Diketotetrahydropyrimidines by Action of a Mixture of Superoxol and Hydrochloric Acid", Jour. Am. Chem. Soc., Vol. 65, pt. 1, pp. 1218–1219 (1943); "Action of Alkali and Ammonia on 2,4-Dialkoxypyrimidines", Jour. Am. Chem. Soc., Vol. 56, pt. 1, pp. 134–139 (1934); "The Reaction of Bromine with uracils", Jour. Org. Chem., Vol. 24, p. 11, Jan., 1959; Wang, "Reaction of Bromine with Uracils", Nature 180, pp. 91–92 (July 13, 1957), and Brown infra.

The reaction of bromine or chlorine with uracil is as follows:

|  |  | H° (K cal/mole) | | |
|---|---|---|---|---|
| X = | F | Cl | Br | I |
| C=C + X$_2$   CX—CX | −107.2 | −33.1 | −18.8 | + 1.2 |
| C−H + X$_2$   C−X+HX | −102.5 | −22.9 | − 6.2 | +13.7 |

Since the carbon-carbon bond energy is only about 60 K cal/mole, it is quite evident that unless the heat of reaction is removed rapidly the heat evolved in fluorination is more than sufficient to destroy the carbon skelton.

A number of methods have been used in which the heat of reaction is dissipated rapidly enough to give fair yields of fluorinated product. The more common methods are: (1) bubbling a mixture of fluorine and an inert gas through a cold liquid; (2) conducting away the heat of reaction by conducting the reaction in the presence of metal packing; and (3) addition of very large amounts of an inert diluent gas. See M. Stacey, J. C. Tatlow, and A. G. Sharpe, "Advances in Fluorine Chem.", Vol. 2, pp. 196–208, Butterworth, Inc., Washington, D.C. (1961); M. Hudlicky, "Chemistry of Organic Fluorine Compounds", The MacMillan Co., New York (1962); and J. H. Simons, "Fluorine Chemistry", Vol. 1, Academic Press, Inc., New York, N.Y. (1950).

An aqueous medium has seldom been used to assist in fluorination of organic compounds. Reference may be made to the work of Banks, Haszeldine and Lalu, Chem. and Ind. (London), 1803 (1964), CA 62, 428 g.

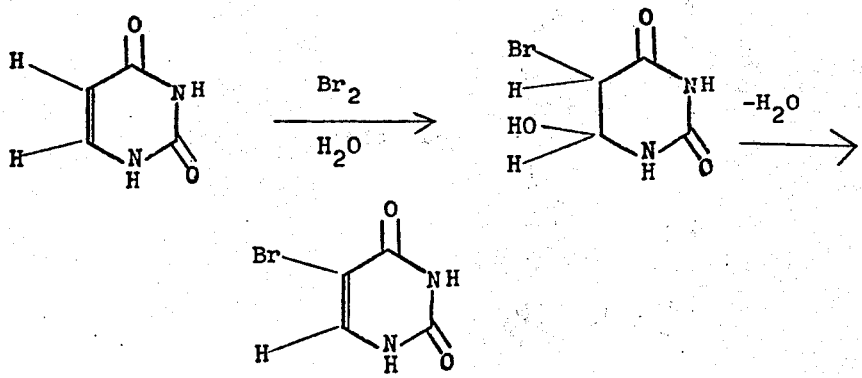

Numerous references may be cited which demonstrate the extreme reactivity of fluorine in contrast to the other halogens. For example, see M. Hudlicky, "Chemistry of Organic Fluorine Compounds", The MacMillan Co., New York (1962), and J. H. Simons, "Fluorine Chemistry", Vol. 1, Academic Press, Inc., New York, New York (1950). This extreme reactivity and the presumed required intermediacy of a hypohalous acid addition to the double bond would preclude the predictability of the reaction product of the aqueous fluorination of uracil.

The reaction of elemental fluorine with organic compounds has been studied extensively since the discovery of the gas by Henri Moissan in 1886. Moissan found that unlike chlorine, bromine and iodine, the unmoderated reaction of fluorine with organic compounds results in ignition and ultimate decomposition of the organic compound to smaller molecules. This greatly increased reactivity of fluorine compared to the other halogens is readily explained by comparing the heats of reaction of the halogens as in the following reactions. See M. Hudlicky, "Chemistry of Organic Fluorine Compounds", p. 72, The MacMillan Co., New York (1962).

(1965), in which esters of carbamic acid were fluorinated.

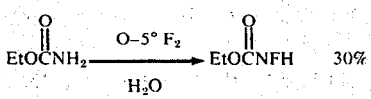

Since uracil exists predominantly in the oxo or keto form, see D. J. Brown, "The Pyrimidines", p. 9, Interscience Publishers, Inc., New York (1962), the results of Bank's work would lead one to believe that fluorination of uracil would result in N fluorination rather than C fluorination, i.e., would yield products containing N-F groups.

It is also known to prepare 5-fluorouracil by reacting uracil mixed with a diluent amount of acetic acid, anhydrous hydrofluoric acid or sulfuric acid and treating the mixture with fluorine mixed with nitrogen as an inert gas at a temperature of 20° to 25°C, see Belgian patent 748,468 to Knuniants et al. However, the yield of 5-fluorouracil produced by this process is generally low and the presence of the diluents in the reaction mixture tends to give rise to undesirable secondary reaction products.

As previously stated, the process of the present invention is useful for the fluorination of uracil to form 5-fluorouracil as well as novel uracil derivatives. The use of 5-fluorouracil in the treatment of cancer, particularly dermatological cancers, is known and well documented. See Heidelberger et al, "Studies on Fluorinated Pyrimidines II — Effects on Transplanted Tumors", Cancer Research, Vol. 18, p. 305 (1958), and Heidelberger et al, "Fluorinated Pyrimidines, A New Class of Tumor-Inhibitory Compounds , Nature, Vol. 179, p. 663, Mar. 30, 1957. Bardos et al, Nature 183, 612 (1959), and Brown, D. J. "The Pyrimidines", p. 175, Interscience, New York (1962).

The commercially employed method for the synthesis of 5-fluorouracil disclosed in U.S. Pat. No. 2,802,005 utilizes extremely toxic monofluoro intermediates. See Stacey et al, "Advances in Fluorine Chemistry", Vol. 2, pp. 196–208, Butterworth, Washington, D.C. (1961). Large scale production has not been undertaken primarily because of the difficulty in handling these intermediates.

It is also known to prepare various uracil derivatives by reacting 5-fluorouracil with chlorine or bromine in the presence of water, as disclosed in Duschinsky et al U.S. Pat. No. 3,277,092. The reaction may be described by the following scheme:

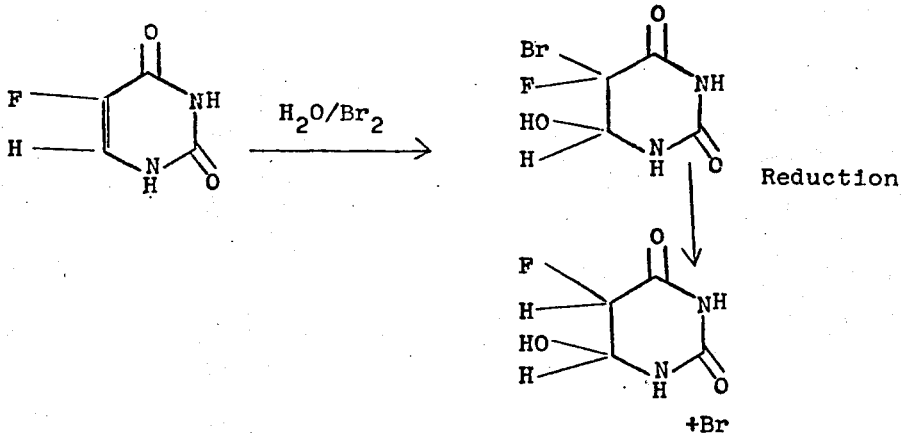

This procedure requires a separate reduction step to remove the bromine, or chlorine, as the case may be, to produce the uracil derivative, in this case 5-fluoro-6-hydroxy-5,6-dihydrouracil.

DETAILED DESCRIPTION OF THE INVENTION

We have found that uracil may be reacted directly with fluorine in an aqueous medium to produce exceptionally high yields of 5-fluorouracil. The fluorine appears to substitute only in the 5-position, and only one fluorine atom is substituted at that site. We do not intend to be bound by any theories; it is possible, however, that the reaction may be expressed according to the following suggested reaction scheme:

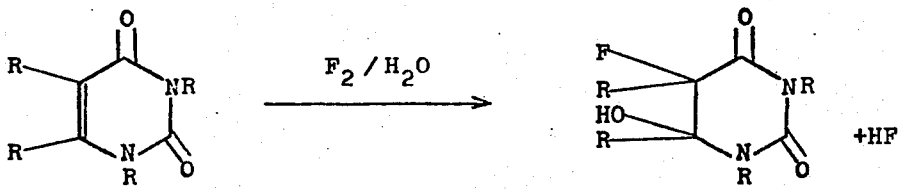

thus giving a reaction product of the addition of FOH to the 5,6-double bond.

The reaction product may then be treated with an alkali, such as an alkali metal hydroxide, e.g., calcium hydroxide, to neutralize the hydrofluoric acid, and the 5-fluorouracil is converted to a salt. Preferably the reaction product is converted into the sodium salt by treating with sodium hydroxide.

According to the present process, 5-fluorouracil and derivatives thereof are prepared by reacting at a temperature of about 9 to 100°C. a uracil derivative of the formula:

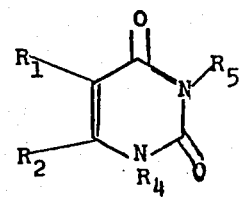

with gaseous fluorine in the presence of water to prepare a compound of the formula:

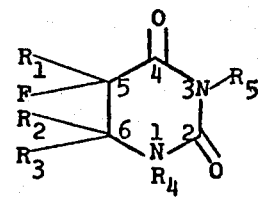

where $R_1$ is hydrogen, haloen, lower alkyl, or, taken with $R_3$, is a 5,6-double bond; $R_2$ is hydrogen, hydroxyl, or lower alkyl; $R_3$ is hydroxyl or taken with $R_1$ is a 5,6-double bond; $R_4$ is hydrogen, or lower alkyl; and $R_5$ is hydrogen or lower alkyl.

As the halogen substituent there may be chlorine, bromine and fluorine. Lower alkyl generally designates an alkyl group having from 1 to 6 carbon atoms such as methyl, ethyl, propyl, butyl, hexyl, etc., and the position isomers thereof, including halogen substituted lower alkyl groups, such as chloroethyl, bromopropyl, etc. The reaction may be conducted over a wide range of temperatures. As aqueous solvents are employed for the reaction mixture, temperatures exceeding the boiling point or below the freezing point of water are not generally used and the reaction temperature is usually maintained within the range of about 9°C to about 100°C; preferably from about 50°C to about 90°C, depending upon the nature of the starting materials employed. The reaction is preferably conducted at atmospheric pressure. Although higher or lower pressures may be used they involve no particular advantage. Fluorine is preferably introduced into the aqueous reaction mixture in an inert gaseous medium such as nitrogen. The ratio of fluorine to nitrogen is preferably within the range of about 1:1 to about 3:1.

As will be obvious from a consideration of the foregoing suggested reaction scheme there is present at least one mole of gaseous fluorine per mole of uracil or derivative thereof. In practice a molar ratio greater than 1:1 is used to assure completion of the reaction, thus a ratio in excess of 1:1, perhaps even a ratio of fluorine to uracil derivative of 2:1 is employed. While greater amounts of fluorine may be used, there is no particular advantage in doing so and greater costs will be incurred. For convenience of determining the completion of fluorination, the reaction may be stopped when fluorine is detected in the reaction gas effluent or shortly thereafter.

The uracil is reacted in the form of an aqueous solution or slurry. The compound 5-fluoro-6-hydroxy-5,6-fluorohydrin and has an elemental analysis of $C_4H_5FN_2O_3$. It is to be noted that the uracil fluorohydrin produced according to the above mentioned patent is not hydrated.

The fluorine gas is preferably bubbled through the solution of uracil, and may be diluted with an inert gas so that it comprises about 10–80%, preferably about 50% by volume of the gas mixture. No evidence has been found which would indicate the presence in the reaction mixture of any compounds containing N-F groups in other than trace amounts. Reaction of fluorine with uracil in solution or as a dispersion in water yields mainly two products, 5-fluorouracil and 5-fluoro-6-hydroxy-5,6-dihydrouracil monohydrate. As sometimes used herein, particularly in Examples 1-14 5-fluoro-6-hydroxy-5,6-dihydrouracil monohydrate is alternatively identified as 5-fluoro-5,6-dihydro-2,4,6,-trihydroxy primidine. The latter compound, also known as uracil fluorohydrin monohydrate, was found to readily revert to 5-fluorouracil by using several techniques such as refluxing a water solution thereof for several hours, simply heating or preferably heating in a stron inorganic acid as hydrochloric, sulfuric and the like. However, it is not known whether uracil fluorohydrin monohydrate is an intermediate in the formation of 5-fluorouracil, or whether it is produced in the same reaction or is not produced until after there is at least some 5-fluorouracil present. It is postulated that the fluorination of other uracil derivatives results in similar intermediate compounds. Thus, in accordance with the process aspect of the present invention, 5-fluorouracil and derivatives thereof are obtained in good yields through direct fluorination of uracil compounds in an aqueous medium. The dehydration of uracil fluorohydrin monohyrate may be illustrated:

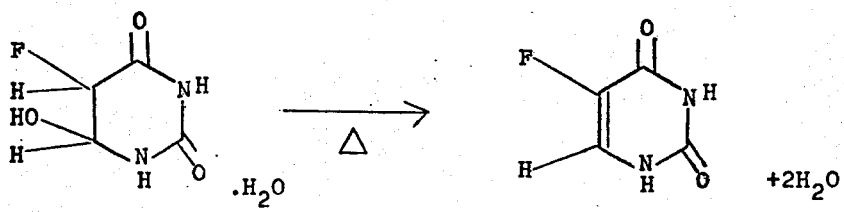

dihydrouracil monohydrate having an elemental analysis of $C_4H_7FN_2O_4$ is produced in the same reaction. On dehydration, this compound yields 5-fluorouracil. The compound 5-fluoro6-hydroxy-5,6-dihydrouracil, also known as 5-fluoro-6-hydroxyhydrouracil, is described in U.S. Pat. No. 3,277,092. It may also be called uracil A particularly interesting reaction occurs in the dehydration of 5,5-difluoro-6-hydroxy-4,5-dihydrouracil wherein the substituted uracil is dehydrated with a mixture of hot trifluoroacetic acid and trifluoroacetic anhydride. Hot hydrochloric acid is not recommended for this dehydration. The reaction scheme is as follows:

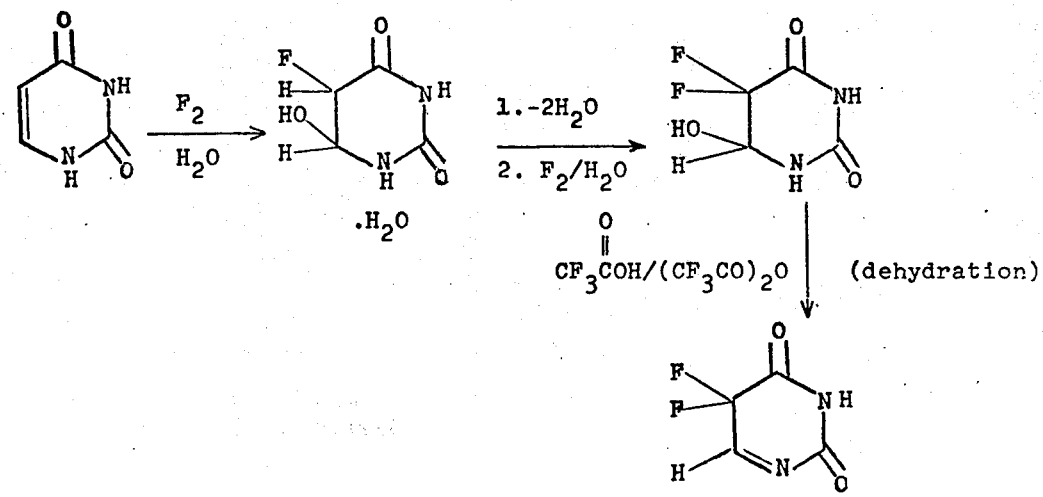

The product of the dehydration reaction was difficult to identify but has tentatively been assigned the above structure.

In the compound aspect of the present invention the above described process produces novel uracil derivatives, among them are compounds having the following general formulas:

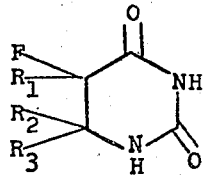

where $R_1$ is hydrogen, fluorine, chlorine or bromine or lower alkyl, $R_2$ is hydrogen and $R_3$ is hydroxyl provided, however, that when $R_1$ is hydrogen, chlorine or bromine, $R_2$ is lower alkyl; and

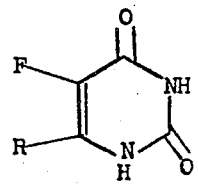

where R is lower alkyl.

From the foregoing description of the process for directly fluorinating uracil derivatives in an aqueous medium, it will be apparent that the compounds of the present invention are conveniently prepared by selection of suitable starting materials. These novel compounds are useful as germicidal agents being active, for example, against gram negative and gram positive bacteria and against yeasts and fungi. This is in agreement with the use of other uracil derivatives disclosed in U.S. Pat. No. 3,277,092, the disclosure of which is hereby incorporated by reference. In addition, certain of the novel compounds of the present invention are believed to exhibit cancerostatic properties, as for instance 5,5-difluoro-6-hydroxy-5,6-dihydrouracil having the structure:

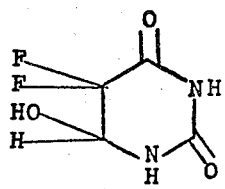

As novel compounds of the present invention there may be mentioned:
5,5-difluoro-6-hydroxy-5,6-dihydrouracil
5-fluoro-5-methyl-6-hydroxy-5,6-dihydrouracil
5-fluoro-5-methyl uracil
5,5-difluoro-6-methyl-6-hydroxy-5,6-dihydrouracil
5-fluoro-6-methyl uracil
5-fluoro-5,6-dimethyl-6-hydroxy-5,6-dihydrouracil

EXAMPLE 1

Into a 500 -ml., 3-neck flask, equipped with a magnetic stirrer, a monel bubbler, and a gas outlet tube leading to a 5% KI indicator solution, was placed 7.34 g. (65mM) of uracil and 250 ml. of distilled water. A tared cylinder of fluorine and a cylinder of nitrogen were connected to the inlet tube. At room temperature, while stirring the uracil dispersion, a mixture of fluorine and notrogen, about equal volumes, was added at a rate of 6.7 g. of fluorine/hr. During addition the temperature of the reaction mixture rose to about 50° and after 5 g. (131 mM) of fluorine was added no dispersed solids remained. Evaporation of the reaction mixture gave 7 g. of crude product which on sublimation at 190°/0.1mm pressure gave 3 g. (23 mM), 35.7% yield, of 5-fluorouracil, m.p. 280°–282°(Lit. value 281°–282°).

EXAMPLE 2

Into a tubular Pyrex reactor 30 mm. by 290 mm. long equipped with a thermometer well, a Teflon bubbler, and a gas outlet tube leading to a 5% KI trap was placed 3 g. (0.027 mole) of uracil and 97 ml. of distilled water. The reactor was heated in a water bath while flushing with nitrogen. When the reaction mixture reached 89° fluorine flow was started at a rate of 11.4 g./hr. with a 1:1 volume ratio of $F_2:N_2$. In six minutes the reaction temperature rose to 92° then dropped to 83° in the final ten minutes. The clear reaction mixture was removed from the reactor, neutralized with calcium carbonate, filtered, and the filtrate evaporated to dryness. Ultraviolet analysis showed a yield of 27% 5-fluorouracil. This example and subsequent examples run in this 100-ml. reactor are summarized in Table 1.

EXAMPLE 3

This example is the same as Example 2 with the exception of gas flow rates. A fluorine rate of 8.0 g./hr. with a 1:1 volume ratio of fluorine to nitrogen was used. The 5-fluorouracil yield was 21%.

EXAMPLE 4

This example is the same as Example 3 with the exception that the fluorine was not diluted with nitrogen. The 5-fluorouracil yield was 27.8%.

EXAMPLE 5

This example is the same as Example 3 with the exception of the amount of uracil fluorinated. Initially 20 g. (0.18 moles) of uracil was dispersed as a slurry at 90°. After 0.26 mole of fluorine was added no solids remained. Yield of 5-fluorouracil was 21%.

EXAMPLE 6

Into a tubular Pyrex reactor 6.0 cm. by 148.5 cm. long equipped with a thermometer well, a sampling outlet, a gas bubbler, and a gas outlet tube leading to a 5% KI trap was placed 112 g. (1.0 mole) of uracil and 3500 ml. of distilled water. The reaction mixture was heated externally while flushing with nitrogen. Whenn the reaction mixture reached 50° fluorine flow was started at a rate of 96 g./hr. with 0.7:1 volume ratio of $F_2:N_2$. With external heating off the reaction temperature rose from 50° to 70° in 84 minutes. The uracil was initially as a dispersion, but after 0.64 moles of $F_2$ was added no solids remained. After 3.0 moles of $F_2$ was added the reaction mixture was removed from the reactor, neutralized with calcium carbonate, filtered, then evaporated under reduced pressure. Crude solids obtained, 110 g., analyzed by ultraviolet as 45.6% 5-flurouracil or 38.5% yield. No unreacted uracil was detected. This example and the following examples are summarized in Table 2.

EXAMPLE 7

This reaction was run in the same reactor as Example 6 with the reactor now equipped with an external cooling coil. Added to the reactor was 454 g. (4.05 moles) of uracil and 3046 ml. of distilled water. The reactor was heated to 70° and fluorine was initially added at a rate of 300 g./hr. An immediate submerged explosion occurred. The fluorine rate was gradually reduced to 168 g./hr. wit a 2:1 volume ratio of $F_2:N_2$. The temperature of the reaction mixture rose from 72° to 89° in 26 minutes and remained at 89° – 92°, with cooling, during the remainder of the reaction. After 168 g. (4.4 moles) of fluorine was added no solids remained. A 50-ml. aliquot was taken after 5.8 moles of fluorine was added. Analysis by thin layer chromatography indicated about a 60/40 minute of uracil to 5-fluorouracil. A 50-ml. aliquot was taken after 8.8 moles of fluorine was added. TLC analysis showed no uracil remaining. An infrared analysis of the dried solids after an ethanol wash was identical to an authentic sample of 5-fluorouracil.

Yield of 5-fluorouracil in this example was 26.8%.

EXAMPLE 8

This example is the same as Example 7 with the exception of the uracil concentration. Aliquot samples were taken at various intervals and analyzed for uracil and 5-fluorouracil. Yield of 5-fluorouracil, 78%, was obtained at a fluorine-to-uracil ratio of 1.67 to 1.

EXAMPLE 9

This example is the same as Example 8 with the exception that the fluorine was added without nitrogen dilution. Aliquot samples were taken at various intervals and analyzed for uracil and 5-fluorouracil. Yield of 5-fluorouracil, 55%, was obtained at a fluorine-to-uracil ratio of 1.67 to 1.

EXAMPLE 10

This example is essentially the same as Example 9 with the exception that the reaction was run at 9° – 13°. After a 1.67 to 1 molar excess of fluorine was added a trace of 5-fluorouracil was detected.

EXAMPLE 11

A 3% dispersion of uracil was fluorinated at 49°–57° at a fluorine rate of 168 g./hr. with a fluorine-to-nitrogen volume ratio of 2:1. Aliquot samples were taken at various intervals and analyzed for uracil and 5-fluorouracil. A yield of 5-fluorouracil, 32.3% was obtained at a fluorine-to-uracil molar ratio of 1.47 to 1.

EXAMPLE 12

This example is essentially the same as Example 9 with the exception that the reaction was run at 50° – 53°. Aliquot samples were taken at various intervals and analyzed for uracil and 5-fluorouracil. A 34.4% yield of 5-fluorouracil was obtained at a fluorine-to-uracil molar ratio of 1.48 to 1.

EXAMPLE 13

This example is essentially the same as Example 11 with the exception that a higher concentration of uracil, 13%, was fluorinated. Aliquot samples were taken at various intervals and analyzed for uracil and 5-fluorouracil. A 35.2% yield of 5-fluorouracil was obtained at a fluorine-to-nitrogen ratio of 1.81 to 1. When the reaction mixture was kept at room temperature overnight in a polyethylene bottle, 41.5g. uracil fluorohydrin precipiated from solution. Upon refluxing with water, the uracil fluorohydrin was converted to 5-fluorouracil.

EXAMPLE 14

Into a vertical, Teflon-lined reactor, 1 11/16 inch I.D. by 10 feet in length, equipped with two gas bubblers located 1 inch and 2 feet from the bottom blind flange was added 520 g. (4.65 moles) of uracil and 3480 g. of distilled water. While bubbling nitrogen through the system at a rate of 0.85 l/min. through each bubbler the slurry was heated by external hot water coils to 50°C.

Fluorine flow was started at 168 g./hr. through the lower bubbler and at 168 g./hr. through the upper bubbler. The reaction temperature rose rapidly to 59°C with occasional submerged explosions occurring. The fluorine rate at the upper bubbler was reduced to 72 g./hr. diluted with nitrogen at 51 l./hr. and the nitrogen rate of the lower bubbler was increased to 120 l./hr. During the course of the reaction the reaction temperature rose to 84°C. The temperature was maintained between 81° and 84°C for the remainder of the reaction.

The addition of fluorine was stopped after 282 g. (7.45 moles) of fluorine was added. The clear reaction solution was cooled to room temperature. On standing 137 g. of pink crystalline uracil fluorohydrin precipitated from solution. The supernatant liquid was decanted and a 25 ml. aliquot evaporated to dryness. Thin layer chromatographic analysis (Silica Gel GF 254, Brinkman Insts. Inc. 10% $C_6H_6$/90% ETO AC, spotted from a 0.1 N $NH_4OH$ solution) indicated the presence of 5-fluorouracil. Ultraviolet analysis indicated the presence only of uracil fluorohydrin monohydrate.

The solid aliquot residue was redissolved in water and heated to 100°C for 48 hours, then evaporated to dryness. The remaining sample, by ultraviolet analysis, was 4.0 grams of 5-fluorouracil.

Various data taken from the examples are set out in Tables I and II. It will be seem from these tables that a wide variety of reaction conditions will produce the desired reaction product. The letters following the example numbers in Table II represent samples taken at different stages of the reaction.

TABLE 1

| Example No. | Wt. % Uracil in Water (moles) | Temp. °C | $F_2$ Rate g./hr. | $F_2:M_2$ Vol. Ratio | Moles $F_2$ Added | % Uracil in Product | % Yield of 5-Fluorouracil |
|---|---|---|---|---|---|---|---|
| 2 | 3% (0.027) | 88–92° | 11.4 | 1:1 | 0.08 | 0 | 27% |
| 3 | 2% (0.027) | 89–92° | 8.0 | 1:1 | 0.08 | 0 | 21% |
| 4 | 3% (0.027) | 90–90° | 8.0 | no $M_2$ | 0.08 | 0 | 27.8% |
| 5 | 20% (0.178) | 85–97° | 8.0 | 1:1 | 0.44 | 0 | 21% |

TABLE 2

| Example No. | Wt. % Uracil in Water (moles) | Temp. °C | $F_2$ Rate g./hr. | $F_2:M_2$ Vol. Ratio | Moles $F_2$ Added | % Uracil In Product | % Yield of 5-Fluorouracil |
|---|---|---|---|---|---|---|---|
| 6 | 3.1% (1.0) | 49–70° | 81.6 | 7:1 | 3 | 0 | 38.5% |
| 7 | 13% (4.00) | 71–85° | 168 | 2:1 | 10 | 0 | 26.8% |
| 8A | 1% (0.31) | 86–90° | 168 | 2:1 | 0.294 | 240 | 38.6% |
| 8B | 1% (0.31) | 90–91° | 168 | 2:1 | 0.516 | trace | 78* |
| 8C | 1% (0.31) | 91–92° | 168 | 2:1 | 0.786 | 0 | 64.2* |
| 9A | 1% (0.31) | 85–88° | 168 | no $M_2$ | 0.294 | 211 | 24.6% |
| 9B | 1% (0.31) | 83–90° | 168 | " | 0.516 | 21.6 | 55* |
| 9C | 1% (0.31) | 90° | 168 | " | 0.781 | 0 | 21.1% |
| 10 | 1% (0.31) | 9–13° | 168 | " | 0.519 | 0 | trace |
| 11A | 3% (1.0) | 49–55° | 168 | 2:1 | 0.774 | 27 | 29% |
| 11B | 3% (1.0) | 55–67° | 168 | 2:1 | 1.47 | 27 | 32.3% |
| 11C | 3% (1.0) | 57–52° | 168 | 2:1 | 2.5 | 0 | 22.6* |
| 12A | 1% (0.31) | 50° | 168 | no $M_2$ | 0.22 | 260 | 25.8% |
| 12B | 1% (0.31) | 50–53° | 168 | " | 0.46 | 240 | 34.4% |
| 13A | 13% (4.06) | 47–57° | 168 | 2:1 | 6.4 | 241 | 8.4 |
| 13B | 13% (4.06) | 57–53° | 168 | 2:1 | 7.37 | 20.5 | 8.1% |
| 13C | 13% (4.06) | 53° | 168 | 2:1 | 7.37 | 0 | 35.2* |

*analysis after refluxing in water for approximately 16 hours.

EXAMPLE 15

Preparation of 5-fluorouracil

In a reaction vessel fitted with a magnetic stirrer, thermometer and outlet tube leading to a 5% KI trap uracil (1.0g) suspended in an aqueous solution of 10% $H_2SO_4$ (10 ml) was reacted with a stream of $F_2/N_2$ having a 1:1 volume ratio of $F_2$ to $N_2$ at 66° to 74°C until $F_2$ was detected. A large portion of the water was evaporated on a rotary evaporator at 70°C. On cooling a yellow solid identified as 5-fluorouracil (0.40g) was obtained.

EXAMPLE 16

Preparation of 5,5-difluoro-6-hydroxy-5,6-dihydro uracil

In a Teflon-lined reactor equipped with a magnetic stirrer, thermometer and outlet tube leading to a 10% KI trap a suspension of 5-fluorouracil (5.0g) in water (50 ml) was introduced and heated to 57° to 63°C while an equal volume flow of $F_2/N_2$ was passed through the reaction mixture. After about 95 minutes the reaction mixture was a clear solution with no remaining solid particles. The reaction solution was then evaporated to dryness at 60°C on a rotary evaporator and the resulting solid dried at 80°C under reduced pressure to give 5.9 grams of 5,5-difluoro-6-hydroxy-5,6-dihydrouracil representing a yield of 92.3% calculated on the 5-fluorouracil.

EXAMPLE 17

Preparation of 5-fluoro-5-methyl-6-hydroxy-5,6-dihydrouracil

Thymine or 5-methyluracil (1.00g, 0.00792 moles) was suspended in water (10 ml) in a reaction vessel fitted with a magnetic stirrer, thermometer and outlet tube leading to a 5% KI trap. The suspension was heated to 65°–66°C and treated with a stream of nitrogen and fluorine in a ratio of 1:1 by volume until the reaction mixture became a clear solution and fluorine was detected in the KI trap. The reaction was completed in 92 minutes and required 0.0188 moles of fluorine representing a molar ratio of fluorine to 5-methyluracil of 2.37.

The product was cooled in iced water, then the water was removed at 60°C under reduced pressure to give an off-white solid (1.32g). Infrared and NMR analysis confirmed the structure to be that of 5-fluoro-5-methyl6-hydroxy-5,6-dihydrouracil.

EXAMPLE 18

Preparation of 5,5-difluoro-6-methyl-6-hydroxy-5,6-dihydrouracil

As in the previous example a suspension of 6methyluracil (4.00g) in water (30 ml) was fluorinated to completion of 60-65°C using an equal volume stream of fluorine and nitrogen gas. On standing over two days large white crystals separated out and the reaction mixture was further cooled in an ice-salt mixture for 1 hour to precipitate further amounts of white solid. The solid material was then filtered and dried in vacuo to give 1.90 grams of white solid which was analyzed by NMR and determined to be 5,5-difluoro-6-methyl-6-hydroxy-5,6-dihydrouracil. It was provisionally concluded that the presence of the methyl group on the number 6 carbon atom facilitated the elimination of water between the 5-6 bond.

EXAMPLE 19

Preparation of 5-fluoro-6-methyl uracil

The preceding example was substantially repeated but at a lower reaction temperature. A suspension of 6-methyl uracil (4.00g) in water (30 ml) was maintained at 0°–10°C and fluorinated with a stream of fluorine and nitrogen, present in equal volumes, until fluorine was detected at the reactor outlet. The reaction mixture was allowed to stand for two days at room temperature and 1.05g of crystals were collected and found to have a different IR spectrum than the starting material. A DSC analysis showed 2 transitions at 313°C and 318°C followed by apparent decomposition. The structure of the product was identified as 5-fluoro-6-methyl uracil by NMR analysis.

EXAMPLE 20

Preparation of 5-bromo-5-fluoro-6-hydroxy-5,6-dihydrouracil

In a suitable reaction vessel equipped with an outlet and a KI trap for detecting the presence of fluorine gas 5-bromouracil (1.00g) was suspended in water (10 ml) and maintained at 63-80°C. The reaction mixture was treated with a stream of $F_2/N_2$, both gases present in a volume ratio of 1:1, for a period of 84 minutes, until $F_2$ was detected at the reactor exit and a clear reaction solution was observed. The water from the aqueous reaction solution was removed by a rotary evaporator at 60°C to give 0.60 grams of 5-bromo-5-fluoro-6-hydroxy-5,6-dihydrouracil.

EXAMPLE 21

Preparation of 5-fluoro-5,6-dimethyl-6-hydroxy-5,6-dihydrouracil

A suspension of 5,6-dimethyluracil (1.0g) and water (10 ml) was placed in a reaction vessel fitted with a magnetic stirrer, thermometer and gas outlet tube leading to a 10% KI trap. The suspension was heated and maintained at about 54°–61°C at which time $F_2/N_2$ gas was bubbled into the suspension until fluorine was detected in the KI trap and the reaction mixture was a clear solution. The reaction mixture was allowed to cool to room temperature and 0.1 g of precipitate was collected by filtration analyzed by and identified by NMR to be 5-fluoro-5,6-dimethyl-6-hydroxy-5,6-dihydrouracil.

EXAMPLE 22

Preparation of 5-chlorouracil

In a suitable reaction vessel as in the previous examples a suspension of uracil (1.00g) in an aqueous solution of 18% HCl (10 ml, representing 5 ml of concentrated HCl and 5 ml of water) was introduced. Gaseous fluorine (0.024 moles) was bubbled through the suspension when the reaction temperature of 72°–80°C was reached. The reaction continued for about 140 minutes until the presence of fluorine was detected leaving the reaction vessel. The ratio of fluorine to uracil was 2.73. During the course of the reaction the odor of chlorine gas was observed. A white solid was present throughout the reaction and a final product of 0.98g was collected by filtration. Elemental analysis of the compound detected no fluorine and indicated the compound to be 5-chlorouracil.

EXAMPLE 23

Preparation of 5-fluorouracil

In a reaction vessel as in the previous examples uracil (1.00g) in an aqueous solution of 10% $H_2SO_4$ (10 ml) was introduced and heated to a temperature of about 66°–74°C. The mixture was then treated by bubbling a stream of fluorine gas and nitrogen gas in equal parts through the mixture until the presence of fluorine was detected and the mixture was a clear solution. The water was evaporated on a rotary evaporator at 70°C. Upon cooling 0.40g of a yellowish solid was obtained and was identified by IR analysis as 5-fluorouracil.

EXAMPLE 24

Preparation of 5,5-difluoro-6-hydroxy-5,6-dihydro uracil

In a Pyrex glass cylinder equipped with a Teflon covered copper gas bubbler a slurry of 5-fluorouracil (17g, 0.13 moles) and water (153 ml) were added. The reactor was placed in a water bath, heated to 45°C and a gaseous mixture of nitrogen to fluorine in a 1:1 ratio was added at the rate of 0.35g of fluorine per minute. Fluorination was continued until the reaction mixture was clear and the gas leaving the glass cylinder indicated excessive amounts of unreacted fluorine. Evaporation of the reaction mixture under vacuum gave 29.9 grams of a mixture of $SiO_2$ and 5,5-difluoro-5,6-dihydro-6-hydroxy uracil which was subsequently separated and analyzed: λ max (0.1 N NaOH), 220 mμ, major IR maxima at 2.92, 5.8, 7.92, 8.42 and 9.1μ and NMR analysis consistant with the assigned structure.

EXAMPLE 25

Preparation of 5-fluorouracil

To a Telfon lined reactor equipped with gas bubbles demineralized water (3.78 l) and uracil (454g) were added.

While bubbling nitrogen through the system at about 260 ml/min. the slurry was heated by an internal Teflon coil to 50°–60°C. Fluorine flow was started at 0.354g/min. from each of 4 bubblers. As the temperature started to rise, water at 0° was passed through the internal coil. The temperature wass maintained between 60° and 70°C throughout the reaction.

The addition of fluorine was stopped after 221g (5.81 moles) were added. The resultant clear solution was removed from the reactor, filtered, then cooled to about 0°C for 18 hours. The white crystalline product was removed by filtration, washed with ice water and dried yielding 192g of uracil fluorohydrin monohydrate. Analysis calculated for a typical sample as $C_4FH_7N_2O_4$: C, 28.91%; F, 11.44; H, 4.21; N, 16.86; O, 38.6. Found: C, 28,48; H, 4.21; N, 16.57.

The uracil fluorohydrin monohydrate was divided into two parts, placed in a Pyrex vessel and con. HCl (100 ml) added to each. The slurry was heated between 90°–100°C for about 15 min. After cooling to 0°, the white solid was removed by filtration and washed with cold water. Several runs were combined, 425g, slurried in demineralized water, filtered then dissolved in demineralized water (3.79 l) at 95°–100°C. The solution was passed through a column of 20g. of Pittsburgh activated carbon SGL. The product was crystallized at 0°, removed by filtration and dried at 100°C yielding 335g of pure (greater than 99%) 5-fluorouracil.

As indicated above, the conditions under which the reaction will take place are quite varied. We consider our invention inclusive of all operable conditions under which fluorine will react with uracil. However, it may be said that we prefer to react the fluorine with a solution of at least 0.01% uracil, although much more concentrated solutions and slurries of uracil may be used; so far as we are aware, there is no upper limit to the concentration of dispersed uracil, but if a high-solids slurry is used, care should be taken to see that all of the uracil is wet. Preferably, at least 10% water, based on the weight of mixture (or a mixture of 90% uracil and 10% water), should be present.

The temperature will preferably be between about 9°C and about 100°C. The temperature appears to be a significant factor in the precentage of uracil fluorohydrin monohydrate present in the reaction product. Higher temperatures result in lower contents of fluorohydrin monohydrate. Where it is desired to completely convert to 5-fluorouracil the reaction product comprising 5-fluorouracil and uracil fluorohydrin monohydrate, we subject the reaction product to a dehydration reaction, preferably by heating, specifically by refluxing in water or heating in strong acid such as concentrated HCl. Evaporation to dryness will accomplish the desired result. The entire reaction product may thus be converted to 5-fluorouracil.

The fluorine may be diluted with any practical amount of inert gas; we have found that a mixture by volume of nine parts nitrogen to one part fluorine is more than enough to insure against the possibility of explosions. Any ratio by volume of nitrogen to fluorine from 9:1 to 1:3 may be used. A volume ratio of nitrogen to fluorine of from 1:1 to 3:1 is preferred. The fluorine need not be diluted at all, but the rate of introduction of fluorine to the reaction zone should be controlled to minimize the possibility of explosion if undiluted fluorine is used.

We have also observed that the danger of overreaction is minimized by controlling the rate of introduction of fluorine gas to the reaction zone. This may be accomplished simply to observing the rate of reaction, as in example 7.

The reaction may be performed in batches or continuously.

Based on the preceding examples it will be apparent that other uracil derivatives are prepared substituting the appropriate material for the starting compound.

In the above-described process when both $R_2$ and $R_3$, as designated in the general formulas of the process of the present invention, are both hydroxy groups, spontaneous dehydration is likely to occur, thus $R_2$ taken with $R_3$ is a =O group.

Although aryl groups have not been discussed in the foregoing detailed description it is possible to have uracil starting materials with aryl groups and substituted aryl groups in the 1, 3, 5 and 6 positions. Representative aryl groups are phenyl and ortho, meta and para substituted phenyl groups such as $NO_2$, $SO_3H$, $SO_3Na$, $NH_2$, OH, halogen and the like. Aqueous fluorination according to the novel process of this invention and the corresponding fluorinated products produced thereby have not been described owing to the commerical unavailability of these aryl-substituted compounds at this time.

As in the direct aqueous fluorination reactions described herein a similar reaction appears to occur in the fluorination of barbituric acid and its derivatives. Although the compounds produced thereby are difficult to identify, the following formula has been assigned:

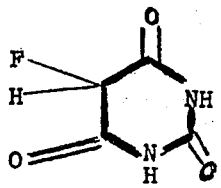

Barbituric acid (20g, 0.0156 moles) suspended in water (20 ml) at room temperature was reacted with a gaseous fluorine: nitrogen mixture for 170 minutes as in the foregoing examples. The temperature of the reaction mixture increased to 65°C. The product was a pale red solution which, upon cooling, gave a white precipitate (0.22g) and the material was tentatively identified as 5-fluorobarbituric acid. Derivatives of barbituric acid could also be fluorinated based on the teaching of the above example.

What is claimed is:

1. Method of making 5-fluorouracil consisting essentially of reacting, in an aqueous medium and at a temperature between about 9°C. and about 100°C., uracil and gaseous fluorine, and dehydrating the resulting reaction product.

2. Method of claim 1, wherein said temperature is about 50°C. to about 9°C.

3. Method of claim 1, wherein the molar ratio of fluorine to uracil is at least 1:1.

4. Method of claim 3, wherein said ratio is 1:1 to 2:1.

5. Method of claim 1, in which the uracil is about 0.01% by weight to about 90% by weight of the total of uracil and water, and the fluorine is diluted with an inert gas at a ratio by volume of inert gas to fluorine of about 9:1 to about 1:3.

6. Method of making 5-fluoro-6-hydroxy-5,6-dihydrouracil monohydrate consisting essentially of reacting gaseous fluorine with uracil at a temperature of about 9°C. to about 100°C. in the presence of water.

7. Method of making 5-fluorouracil consisting essentially of reacting fluorine and uracil in an aqueous medium at a temperature of about 9°C. to about 100°C. to form a reaction product comprising 5-fluoro-6-hydroxy-5,6-dihydrouracil monohydrate, and dehydrating the 5-fluoro-6-hydroxy-5,6-dihydrouracil monohydrate to form 5-fluorouracil.

8. Method of claim 7 in which the reaction product is dehydrated by heating in the presence of a strong inorganic acid.

9. Method of claim 7 in which the dehydration step is performed by refluxing an aqueous solution of said 5-fluoro-6-hydroxy-5,6-dihydrouracil monohydrate.

10. A process consisting essentially of reacting at a temperature of about 9 to 100°C. a uracil derivative of the formula:

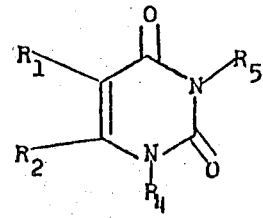

with gaseous fluorine in the presence of water to prepare a compound of the general formula:

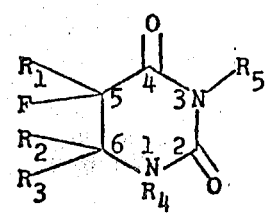

wherein $R_1$ is hydrogen, halogen, lower alkyl, or taken with $R_3$ is a 5,6 double bond;

$R_2$ is hydrogen, hydroxyl or lower alkyl;

$R_3$ is hydroxyl or taken with $R_1$ is a 5,6 double bond provided, however, that when both $R_2$ and $R_3$ are hydroxyl, then $R_2$ taken with $R_3$ is =O;

$R_4$ is hydrogen or lower alkyl, and $R_5$ is hydrogen or lower alkyl.

* * * * *

UNITED STATES PATENT AND TRADEMARK OFFICE
CERTIFICATE OF CORRECTION

PATENT NO. : 3,954,758
DATED : May 4, 1976
INVENTOR(S) : Paul D. Schuman et al

It is certified that error appears in the above-identified patent and that said Letters Patent are hereby corrected as shown below:

Column 4, line 57, delete "haloen" and insert --halogen--.

Column 6, line 19, delete "primidine" and insert --pyrimidine--.

line 24, delete "stron" and insert --strong--.

Column 8, line 18, delete "notrogen" and insert --nitrogen--.

Column 9, line 1, delete "Whenn" and insert --When--.

line 26, delete "wit" and insert --with--.

Column 10, line 22, delete "precipiated" and insert --precipitated--.

Column 11-12, in Table 1, in the heading of fifth column, change "$M_2$" to --$N_2$--; in Table 2, in the heading of fifth column, change "$M_2$" to --$N_2$--.

Table 2, seventh column, line 3, change "240" to --∿40--;

line 6, change "211" to --∿11--;

line 7, change "21.6" to --∿1.6--;

line 10, change "27" to --∿7--;

line 11, change "27" to --∿7--;

UNITED STATES PATENT AND TRADEMARK OFFICE
CERTIFICATE OF CORRECTION

PATENT NO. : 3,954,758
DATED : May 4, 1976
INVENTOR(S) : Paul D. Schuman et al

It is certified that error appears in the above-identified patent and that said Letters Patent are hereby corrected as shown below:

Table 2, seventh column, line 13, change "260" to --∿60--;

line 14, change "240" to --∿40--;

line 15, change "241" to --∿41--;

line 16, change "20.5" to --∿0.5--.

Column 12, line 41, delete entire line and insert therefor --methyl-6-hydroxy-5,6-dihydrouracil.--

Column 12, line 46, delete "6me-" and insert --6-me- --.

line 49, delete "of" (first occurrence) and insert --at--.

Column 14, line 28, delete "bubbles" and insert --bubblers--.

Column 16, line 18, delete "9°C" and insert --90°C--.

Signed and Sealed this

Fifth Day of October 1976

[SEAL]

Attest:

RUTH C. MASON
*Attesting Officer*

C. MARSHALL DANN
*Commissioner of Patents and Trademarks*